(12) United States Patent
Khosravi Simchi et al.

(10) Patent No.: US 10,667,694 B2
(45) Date of Patent: *Jun. 2, 2020

(54) APPARATUS FOR IMAGING SKIN

(71) Applicant: MetaOptima Technology Inc., Vancouver (CA)

(72) Inventors: Sepideh Khosravi Simchi, Vancouver (CA); Maryam Sadeghi, Vancouver (CA); Majid Razmara, Vancouver (CA); M. Stella Atkins, Vancouver (CA)

(73) Assignee: MetaOptima Technology Inc., Vancouver (CA)

( * ) Notice: Subject to any disclaimer, the term of this patent is extended or adjusted under 35 U.S.C. 154(b) by 0 days.

This patent is subject to a terminal disclaimer.

(21) Appl. No.: 16/525,235

(22) Filed: Jul. 29, 2019

(65) Prior Publication Data
US 2019/0343396 A1   Nov. 14, 2019

Related U.S. Application Data

(63) Continuation of application No. 15/568,273, filed as application No. PCT/CA2016/050743 on Jun. 23, 2016, now Pat. No. 10,405,752.
(Continued)

(51) Int. Cl.
*A61B 5/00* (2006.01)
*G03B 15/05* (2006.01)
(Continued)

(52) U.S. Cl.
CPC .......... *A61B 5/0077* (2013.01); *A61B 5/0082* (2013.01); *A61B 5/444* (2013.01); *A61B 5/6898* (2013.01); *A61B 90/36* (2016.02); *G03B 15/05* (2013.01); *G03B 17/565* (2013.01); *G03B 17/566* (2013.01); *G03B 2215/0575* (2013.01)

(58) Field of Classification Search
CPC ..... A61B 5/0077; A61B 5/0082; A61B 5/444; A61B 5/6898; G03B 15/05; G03B 17/565; G03B 17/566; G03B 15/0575
See application file for complete search history.

(56) References Cited

U.S. PATENT DOCUMENTS 8,639,106 B1    1/2014  Gleason et al.
2012/0182620 A1  7/2012  Le et al.
(Continued)

FOREIGN PATENT DOCUMENTS

DE    10146158 A1    4/2003
JP    2011-123085 A   6/2011
WO   2010110096 A1    9/2010

*Primary Examiner* — Twyler L Haskins
*Assistant Examiner* — Fayez Bhuiyan
(74) *Attorney, Agent, or Firm* — Oyen Wiggs Green & Mutala LLP

(57) ABSTRACT

An apparatus for skin imaging is provided. The apparatus is used in conjunction with a mobile device to obtain digital images using a digital camera and a light source provided by the mobile device. The apparatus includes an optical system for illuminating an object to be imaged with uniform ambient light and a light conduit for delivering reflected light to the mobile device digital camera. The apparatus is removably attachable to the mobile device and/or a mobile device case. One or more optical elements, such as lenses, films, filters, and light caps may be used to improve image quality and/or acquire magnified images.

20 Claims, 10 Drawing Sheets

Related U.S. Application Data

(60) Provisional application No. 62/183,713, filed on Jun. 23, 2015.

(51) Int. Cl.
*G03B 17/56* (2006.01)
*A61B 90/00* (2016.01)

(56) References Cited

U.S. PATENT DOCUMENTS

| | | |
|---|---|---|
| 2013/0300919 A1 | 11/2013 | Fletcher et al. |
| 2015/0065803 A1 | 3/2015 | Douglas et al. |

APPARATUS FOR IMAGING SKIN

REFERENCE TO RELATED APPLICATIONS

This application is a continuation application of co-pending U.S. patent application Ser. No. 15/568,273, entitled APPARATUS FOR IMAGING SKIN, filed on Oct. 20, 2017, which was the National Stage of International Application No. PCT/CA2016/050743, entitled APPARATUS FOR IMAGING SKIN, filed on Jun. 23, 2016, which claims the benefit of U.S. Provisional Application Ser. No. 62/183,713, entitled SMART DERMOSCOPE APPARATUS AND SOFTWARE FOR SKIN IMAGING, filed Jun. 23, 2015, which are hereby incorporated herein by this reference in their entirety for all purposes.

TECHNICAL FIELD

This application relates to apparatus useful for imaging skin. Example embodiments provide apparatus that are used in conjunction with mobile devices to obtain digital images using an imaging system and a light source provided by the mobile device.

BACKGROUND

A skin lesion is a part of the skin that has an abnormal appearance compared to the skin around it. Dermoscopy is the evaluation of skin lesions by a specialist with the aid of a dermoscope to diagnose and treat skin conditions and diseases. Typical dermoscopes include a magnifying lens, a non-polarized light source, a contact plate, and a liquid medium that is applied between the contact plate and the skin. The liquid medium reduces light that is reflected from the surface of the skin and allows visual inspection substantially unobstructed by reflected light. Dermoscopes that use polarized light are able to dispense with the liquid medium while cancelling out skin surface reflections. Some dermoscopes are capable of capturing images or video for diagnosis and analysis purposes.

Performed regularly, self-examination can alert an individual to changes in the skin and aid in the early detection of skin conditions and diseases. However, naked eye examination lacks the sensitivity required for early-stage detection of some skin conditions and diseases, e.g. skin cancer. Dermoscopes offer improved sensitivity, but such devices are typically expensive and/or most individuals lack the specialized training in dermatoscopy necessary to distinguish benign from problematic skin lesions.

Mobile devices offer another tool for acquiring images. Many mobile devices today include a digital camera, a light source for illuminating objects in the field of view of the camera, and software for recording, storing, and modifying digital images. However, such devices are typically provided with lenses that have limited ability to magnify small objects such as details of skin lesions. These devices are not suited for imaging small objects or objects under the surface of the skin.

Since it is typically not possible to change the lens of conventional mobile devices, a magnifying lens must be connected to the device to obtain high quality and/or magnified digital images. Lens devices that are removably attachable to mobile devices are known; however, such devices typically include a light source and power supply (such as a battery). For example, some removably-attachable lens devices (such as MoleScope™, HUD™ by First Derm™, and DermLite DL1™) include one or more light emitting diodes (LEDs) positioned about a device lens, rechargeable or disposable batteries to power the LEDs, and complex printed circuit boards to control lighting. Such devices can be undesirable complex, heavy, and/or expensive. Other lens devices use specifically designed solid light guides to collect light from a mobile device light source and are attached to mobile devices cases, for example, as described in Patent publication No. US-2015-0065803 which provides a device for imaging the tympanic membrane that may be used in conjunction with a camera of a cellular telephone.

Mobile device technology is rapidly evolving. With advancements in this field of technology and in consumer preferences, the sizes and shapes of mobile devices rapidly change rendering mobile device cases obsolete. The positions of the mobile device lens and light source also change as the size and shape of mobile devices change.

The foregoing examples of the related art and limitations related thereto are intended to be illustrative and not exclusive. Other limitations of the related art will become apparent to those of skill in the art upon a reading of the specification and a study of the drawings.

SUMMARY

The following embodiments and aspects thereof are described and illustrated in conjunction with systems, tools, and methods which are meant to be exemplary and illustrative, not limiting in scope. In various embodiments, one or more of the above-described problems have been reduced or eliminated, while other embodiments are directed to other improvements.

One aspect of the present invention provides an apparatus for use with a mobile device. The apparatus includes a body and a connector. The body includes a first end defining a first aperture and a second end opposed to the first end, the second end defining a lens aperture and a light guide aperture. The lens aperture is configured to align with a mobile device lens and the light guide aperture is configured to align with a mobile device light source when the apparatus is removably attached to the mobile device. The body comprises an optical system for illuminating an object to be imaged and a light conduit for delivering light reflected by the object to the mobile device lens. The connector is coupled to the body and is adapted for removably attaching the apparatus to the mobile device.

In some embodiments, the optical system includes a beam splitter positioned in front of the light guide aperture. The beam splitter splits light received from the mobile device light source into plural beams and directs the beams in desired directions. In some embodiments the beam splitter is arranged to direct the plural beams into one or more light guides and the one or more light guides distribute light of the one or more beams to illuminate skin or another object to be imaged.

In some embodiments, the beam splitter comprises a prism light guide.

In some embodiments, the beam splitter comprises a light reflector.

In some embodiments, the light reflector comprises a V-shaped mirror.

In some embodiments, the optical system comprises a light guide that extends around the light conduit. The light guide may have a generally circular configuration, for example the light guide may be toroidal or partial toroidal. The light guide may be solid or hollow. A hollow light guide has the advantage of light weight. The optical system may be arranged such that the light guide emits substantially uniform illumination around the circumference of the light conduit.

In some embodiments, a partially toroidal light guide comprises a reflective interior surface and an annular opening for allowing light to exit therefrom.

In some embodiments, the light guide comprises a solid toroidal light guide arranged for uniformly distributing light from the mobile device light source.

In some embodiments, the solid toroidal light guide comprises a first flat surface for allowing light to exit therefrom and a second flat surface for capturing light from the light source aperture.

In some embodiments, the solid toroidal light guide comprises an outer surface coated with a material having a refractive index that is greater than the refractive index of the toroidal light guide.

In some embodiments, the toroidal light guide comprises a diffused surface and/or a diffuser film adjacent to the first flat surface for controlling the amount of light that exits the toroidal light guide and/or for enhancing uniform light distribution.

In some embodiments, the optical system comprises fiber-optic light guide for uniformly distributing light from the mobile device light source.

In some embodiments, the fiber-optic light guide includes a plurality of fibre-optic fibers that merge at the light guide aperture to capture light from the mobile device light source.

The plurality of fibers may be circumferentially distributed about the light conduit. The plurality of fibers may each be coated with a material having a refractive index that is greater than the refractive index of each fiber.

In some embodiments, the apparatus includes an eye cap removably attachable to the first end of the body.

In some embodiments, the apparatus includes an ear cap removably attachable to the first end of the body.

In some embodiments, the body comprises a light cap for uniformly mixing light from the optical system. A distance between a first end of the light cap and a second end of the light cap opposed to the first end may be selected to mix the light uniformly.

In some embodiments, an interior surface of the light cap is coated with a light-absorptive material. The light cap may include a reference ruler and/or a reference colour chart.

In some embodiments, the light conduit includes at least one lens.

In some embodiments, an interior surface of the light conduit is coated with a light-absorptive material.

In some embodiments, the connector includes a bracket extending outwardly from the second end of the body. The bracket defines a first opening between the bracket and the body for receiving the mobile device.

In some embodiments, the bracket is removably attachable to the second end of the body.

In some embodiments, the connector comprises a plurality of brackets. Each bracket may be removably attachable to the second end of the body. Each bracket may extend outwardly from the second end of the body to define an opening between the bracket and the body for receiving the mobile device.

In some embodiments, the connector includes an adapter configured to friction-fit inside the first opening. The adapter defines a second opening for receiving the mobile device.

In some embodiments, the connector includes a plurality of adapters. Each adaptor may be configured to friction-fit inside the first opening and defining a second opening for receiving the mobile device.

In some embodiments, the adapter is C-shaped and defines an aperture configured to align with the first aperture of the body and the mobile device lens.

In some embodiments, the apparatus comprises a mobile device case. The connector may include a magnetic piece that is magnetically attracted to the case for removably attaching the apparatus to the mobile device case.

In some embodiments, the mobile device case defines an aperture configured to align with the mobile device lens and the mobile device light source when the mobile device is inserted into the case.

In some embodiments, the mobile device case includes a magnetic piece adjacent to the aperture for aligning the mobile device lens with the lens aperture and the mobile device light source with the light source aperture.

In some embodiments, the apparatus further includes at least one filter. The at least one filter may comprise a diffuser film and/or a first polarizer filter and/or a second polarizer filter.

In some embodiments, first and second linear polarizers are arranged with their polarization axes at 90 degrees to one another.

In some embodiments, circular polarization is used, a first polarizer filter is polarized in a clockwise direction and a second polarizer filter is polarized in a counterclockwise direction or vice versa.

In some embodiments, the at least one filter comprises a filter configured for providing structured precision lighting.

In some embodiments, the apparatus includes a contact lens removably attachable to the first end of the body. The contact lens may be disposable and/or magnifying.

Another aspect of the present invention provides an apparatus for use with a mobile device. The apparatus includes an optical system for illuminating an object to be imaged with light from a mobile device light source, a light conduit for delivering light reflected by the object to a mobile device lens, and a connector for removably attaching the apparatus to the mobile device.

In some embodiments, the light conduit comprises at least one lens.

One aspect of the invention provides a compact device that collects light in a relatively small area and distributes the light to provide uniform illumination emanating from an annular area. Such a device may be applied to collect light from a flash or other illumination source of a mobile device such as a cellular telephone and to distribute that light from an annulus surrounding a lens of a camera of the mobile device. Such an arrangement can be useful for close-up photography using the camera. The device may project a relatively small distance (e.g. 15 mm or less—in some embodiments 11 mm or less) from a surface of the mobile device.

In some embodiments light from the light source of the mobile device is split by a beam splitter into plural light beams that are directed into one or more light guides. The one or more light guides may extend in a plane that is perpendicular to an optical axis of the camera of the mobile device. In some embodiments the one or more light guides extend along a circular path concentric with the optical axis of the mobile device. In some embodiments the beam splitter is integrated with a light guide that collects light from the light source of the mobile device.

In addition to the exemplary aspects and embodiments described above, further aspects and embodiments will become apparent by reference to the drawings and by study of the following detailed descriptions.

BRIEF DESCRIPTION OF THE DRAWINGS

Exemplary embodiments are illustrated in referenced figures of the drawings. It is intended that the embodiments and figures disclosed herein are to be considered illustrative rather than restrictive.

DESCRIPTION

Figure 1:
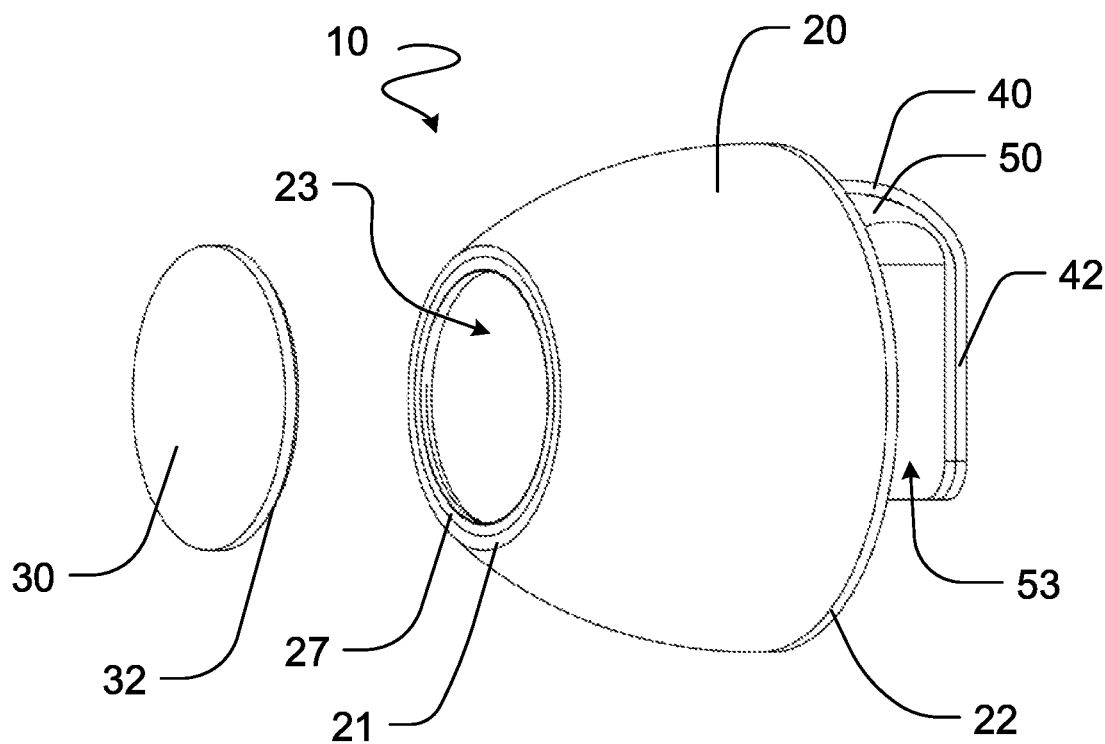
FIG. 1 is a front perspective view of an apparatus for imaging skin according to an example embodiment of the present invention.
Figure 2:
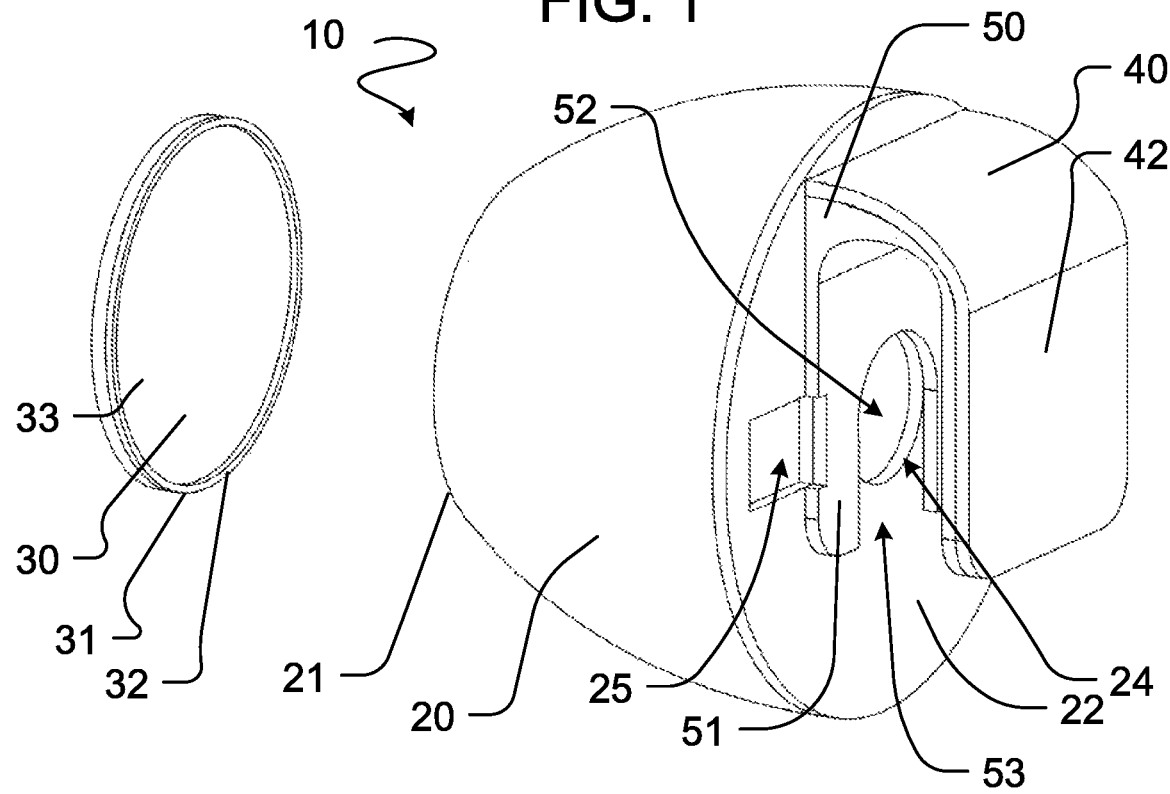
FIG. 2 is a rear perspective view of the apparatus shown in FIG. 1.

Throughout the following description specific details are set forth in order to provide a more thorough understanding to persons skilled in the art. However, well known elements may not have been shown or described in detail to avoid unnecessarily obscuring the disclosure. Accordingly, the description and drawings are to be regarded in an illustrative, rather than a restrictive, sense.

Unless the context dictates otherwise, "mobile device" (as used herein) refers to a handheld computer including a digital camera and a light source. For example, a mobile device may comprise a smartphone, a tablet computer, and/or a personal digital assistant (PDA).

Unless the context dictates otherwise, "digital camera" (as used herein) refers to a device comprising an imaging system for digitally encoding images and/or videos. The digital camera may internally store the images and/or videos or transmit the images and/or videos to an external storage device for storage, reproduction, viewing, and/or modification.

Unless the context dictates otherwise, "imaging system" (as used herein) refers the combination of an optical sensor and an optical system for acquiring digital images.

Unless the context dictates otherwise, "optical sensor" (as used herein) refers to a mobile device sensor that measures the intensity of electromagnetic waves typically in a wavelength range between UV light and infrared light. For example, an optical sensor may comprise a photodiode.

Unless the context dictates otherwise, "optical system" (as used herein) refers to a system that includes one or more of lenses, mirrors, reflectors, filters, prisms, optical gaps and light guides.

Unless the context dictates otherwise, "light guide" (as used herein) refers to an apparatus that is capable of carrying light from one location to another. A light guide may include, but is not limited to, one or more of optical fibers and hollow or solid geometric shapes that internally reflect light.

Unless the context dictates otherwise, "light source" (as used herein) refers to an electronically-powered device that emits photons to provide illumination and includes, but is not limited to, LEDs.

Unless the context dictates otherwise, "optical element" (as used herein) includes a lens, a mirror, a reflector, a filter, a prism, a light guide, or an optical film.

Unless the context dictates otherwise, "optical aberration" (as used herein) refers to a departure of the performance of an optical system from the paraxial approximation. For example, in an imaging system, optical aberration occurs when light from one point of an object does not convert into (or does not diverge from) a single point after transmission through the system.

Unless the context dictates otherwise, "paraxial approximation" (as used herein) refers to a small-angle approximation used in Gaussian optics for tracing light rays through an optical system. A light ray that is paraxial makes a small angle to an optical axis of an optical system and lies close to the axis throughout the system.

Unless the context dictates otherwise, "field of view" (as used herein) refers to the extent of the observable world that is seen (by eye, imaging system, or optical sensor) at a given moment. In the case of an imaging system and/or sensor, field of view refers to the range of angles through which an optical sensor is sensitive to electromagnetic radiation.

Unless the context dictates otherwise, "focal length" (as used herein) refers to the distance between a lens and a focal point of an optical system, wherein the lens converges parallel rays of light into the optical system's focal point). The focal length of an optical system is a measure of how strongly the system converges or diverges light. A system with a shorter focal length has greater optical power than one with a longer focal length since the system with the shorter focal length is able to bring light rays into focus in a shorter distance.

Unless the context dictates otherwise, "f-number" (as used herein) refers to the ratio of the focal length of a lens to the diameter of an aperture of an optical system. It is a dimensionless number that is a quantitative measure of, for example, camera lens speed.

Unless the context dictates otherwise, "angle of incidence" (as used herein) refers to an angle between a light ray incident on a surface and a line perpendicular to the surface at the point of incidence.

Unless the context dictates otherwise, "angular distribution" (as used herein) refers to the distribution of light emitted by a light source over angles ranging from 0° to 360° relative to a specified angle (for example, relative to 0°).

Unless the context dictates otherwise, "uniform light distribution" (as used herein) refers to a distribution of light such that over an area of interest there is a substantially uniform light level.

Unless the context dictates otherwise, "optical magnification" (as used herein) refers to the ratio between a dimension of an object in an image and the corresponding dimension of the object itself. Optical magnification is a dimensionless number.

Unless the context dictates otherwise, "structured precision lighting" (as used herein) refers to light projected in a known pattern (i.e. a plane, a grid, or a more complex shape) at a known angle.

Unless the context dictates otherwise, "specular reflection" (as used herein) refers to a mirror-like reflection of light from a surface, in which the angle of reflection equals the angle of incidence. The incident ray, the reflected ray, and the normal direction are copolanar.

Unless the context dictates otherwise, "diffuse reflection" (as used herein) refers to a reflection of light from a surface such that an incident ray is reflected at many angles rather than at just one angle (as in the case of specular reflection).

Unless the context dictates otherwise, "diffuser" (as used herein) refers to a filter that diffuses or scatters light in some manner A diffuser may be applied to provide soft light and/or to achieve a more uniform light distribution.

Unless the context dictates otherwise, a "polarizer" (as used herein) refers to an optical filter that can convert a beam of light of undefined or mixed polarization into a beam of well-defined polarization.

Unless the context dictates otherwise, "linear polarizer" (as used herein) refers to a polarizer that selectively passes or creates a linearly-polarized electromagnetic wave (e.g. a linearly-polarized light wave). The direction of the electric field of the electromagnetic wave is aligned parallel to a polarization direction or 'polarization axis' of the polarizer.

Unless the context dictates otherwise, "circular polarizer" (as used herein) refers to a polarizer filter that selectively passes and/or creates a circularly-polarized electromagnetic wave. In a circularly-polarized wave a direction of the electric component of the electromagnetic wave changes in a rotary manner along the direction of propagation. Circular polarization can be either clockwise or counterclockwise.

Unless the context dictates otherwise, "beam splitter" (as used herein) refers to an optical device that is operable to split a beam of light into plural beams of light.

Unless the context dictates otherwise, "Total Internal Reflection" (as used herein) refers to a phenomenon which occurs when a wave propagating in a first medium strikes a boundary of the first medium with a second medium and the wave is entirely reflected back toward the first medium. Total internal reflection can occur when the second medium has lower index of refraction and the angle of incidence of the wave with the boundary is larger than a critical angle.

Some embodiments of the present invention provide an apparatus for skin imaging. The apparatus is used in conjunction with a mobile device to obtain digital images using a digital camera and a light source provided by the mobile device. The apparatus captures light from the mobile device light source and delivers light that is suitable for imaging skin, including skin lesions and/or features below the surface of the skin, to illuminate skin to be imaged. Light reflected and/or scattered from the skin surface re-enters the apparatus and is delivered to a lens of the mobile device digital camera. The apparatus is removably attachable to the mobile device and/or a mobile device case. One or more optical elements, such as prisms, reflectors, and light guides, are used to deliver light from the mobile device light source to the skin. The apparatus may include one or more optical elements, such as lenses, films, and/or filters, and/or a light cap for improving image quality and/or for acquiring magnified digital images.

The optical system that captures light from the mobile device and distributes that light in a manner suitable for acquiring images of skin or another object may be relatively very compact. Various example embodiments are described herein. In some embodiments the apparatus projects by 15 mm or less (in some embodiments 11 mm or less) from a surface of the mobile device (e.g. from a face of a mobile telephone).

An apparatus 10 in accordance with one example embodiment of the present invention is shown in FIGS. 1 to 5. Apparatus 10 may be used in conjunction with any of a variety of mobile devices, such as mobile device 90 (see FIGS. 3 to 5), having a digital camera and a light source to produce digital images of an object. Apparatus 10 includes an optical system for illuminating an object to be imaged with uniform light. Apparatus 10 further includes light conduit for delivering light reflected from the object to the mobile device digital camera. In combination with the digital camera of the mobile device, apparatus 10 may be used to produce digital images that are magnified and/or substantially unobstructed by reflected ambient and/or stray light. Apparatus 10 may include a connector for attaching the apparatus to the mobile device and/or a mobile device case.

Apparatus 10 includes a body 20 that houses the optical system. Body 20 has a first end 21 and a second end 22 opposed to first end 21. Light from a mobile device light source enters body 20 via an aperture 25 defined by second end 22. Light travels through and exits body 20 via an aperture 23 defined by first end 21. Light is reflected by the skin of a subject and reenters body 20 via aperture 23. Body 20 delivers the reflected light, to a lens of a mobile device digital camera via an aperture 24 defined by second end 22. Apertures 24 and 25 are positioned to align with the lens and the light source, respectively, of the mobile device when apparatus 10 is removably attached thereto and/or to a mobile device case attached to the mobile device.

Body 20 is made of a light-weight material, including but not limited to plastic or metal. In some embodiments, body 20 is conical and tapers from second end 22 to first end 21. In some embodiments, body 20 is elliptical and tapers from second end 22 to first end 21. Body 20 may have any shape provided the field of view of apparatus 10 is smaller than the area of second end 22 so that glare effects may be minimized In some embodiments, body 20 includes a bracket, such as bracket 40, for removably mounting apparatus 10 to a mobile device. Bracket 40 extends outwardly from second end 22 of body 20. The mobile device is friction-fit into an opening 41 defined between bracket 40 and second end 22 of body 20 (see FIG. 4). An arm 42 of bracket 40 extends over a front surface of the mobile device when apparatus 10 is removably attached thereto.

Arm 42 may be resilient so as to grippingly engage mobile devices of a range of thicknesses. When the mobile device is fit into opening 41, the lens and the light source of the mobile device concentrically-align with apertures 24 and 25, respectively, of body 20. In this way, optical aberration is minimized The size, shape, and configuration of bracket 40 may be selected to accommodate the various sizes, shapes, and configurations of a mobile device such that apparatus 10 is removably attachable to a variety of mobile devices. For example, opening 41 may be sized, shaped, and/or configured accordingly to fit thicker or thinner mobile devices.

Arm 42 may have different sizes, shapes, and/or configurations for supporting a mobile device. Bracket 40 may be removably attachable to second end 22 of apparatus 10. Apparatus 10 may include a plurality of brackets 40, each bracket removably attachable to second end 22 of body 20 and having a different size, shape, and/or configuration.

In some embodiments, such as the example embodiment shown in FIGS. 1 to 5, apparatus 10 includes an adapter 50 for use with bracket 40 to accommodate the variety of sizes, shapes, and configurations of mobile devices. Adapter 50 is friction-fit into opening 41 and the mobile device is friction-fit into an opening 53 defined by adapter 50, as best seen in the example embodiment shown in FIGS. 3 to 5. Adapter 50 may be C-shaped. An arm 51 of C-shaped adapter 50 may define an aperture 52, which is positioned to concentrically-align with aperture 24 of body 20 when adapter 50 is friction-fit into opening 41. When the mobile device is fit into opening 53 of adapter 50, the lens and the light source of the mobile device concentrically-align with apertures 24 and 25, respectively, of body 20.

The size, shape, and configuration of adapter 50 may be configured to accommodate the various sizes, shapes, and configurations of a mobile device such that apparatus 10 is removably attachable to a variety of mobile devices. For example, arm 51 and/or opening 53 may be sized, shaped, and/or configured to fit thicker or thinner mobile devices. Aperture 52 may be sized, shaped, and/or configured to concentrically-align with the lenses of different mobile devices.

Bracket 40 may be made of a light-weight material including, but not limited to, plastic or metal. In some embodiments, bracket 40 is made of a flexible, but firm, elastic material including, but not limited to, rubber. Adapter 50 may be made of an elastic material, including but not limited to rubber.

Figure 6:
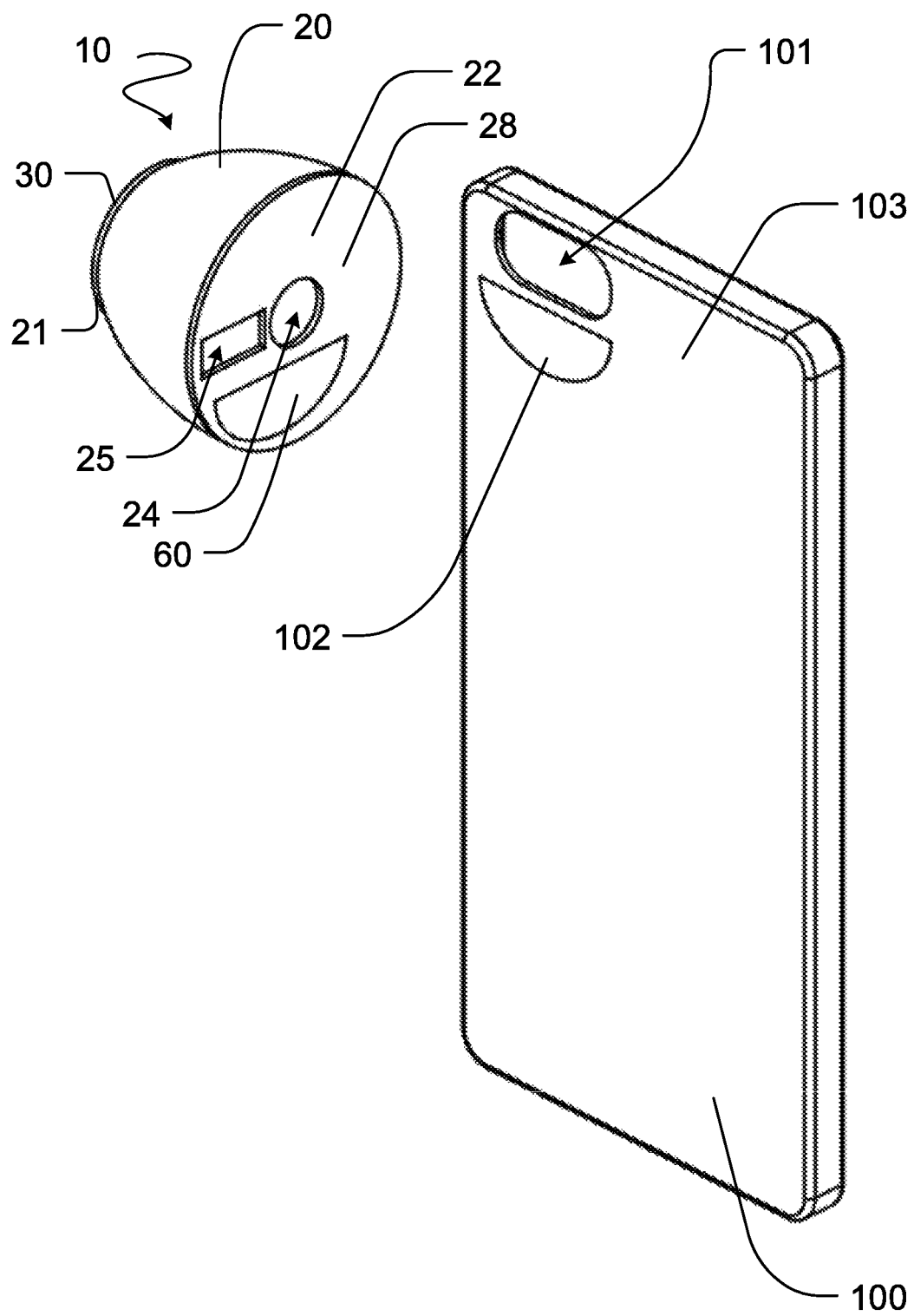
FIG. 6 is a rear perspective view of an apparatus for imaging skin according to an example embodiment of the present invention, wherein the apparatus is removably attachable to a mobile device case.

In the example embodiment shown in FIG. 6, apparatus 10 is removably attachable to a mobile device case using a magnet 60 secured to an outer surface 28 of second end 22 of body 20. In some embodiments, the case is ferromagnetic and apparatus 10 may be removably secured thereto via magnet 60. In some other embodiments, the case, such as mobile device case 100, includes a piece of ferromagnetic material 102 secured to an outer surface 103 thereof for removably attaching apparatus 10 via magnet 60. Case 100 defines an aperture 101, which is positioned to align with the lens and the light source of a mobile device when the mobile device is attached to case 100 (e.g. by being friction-fit inside the cavity (not shown) defined by case 100). Ferromagnetic material 102 is positioned on case 100 adjacent to aperture 101 such that the lens and light source of a mobile device align with apertures 24 and 25, respectively, of apparatus 10 to minimize optical aberration when apparatus 10 is removably attached to case 100. In some embodiments, apparatus 10 includes a lens as described elsewhere herein. Ferromagnetic material 102 is positioned on case 100 such that the mobile device lens concentrically-aligns with the lens of apparatus 10 to minimize optical aberration when apparatus 10 is removably attached to case 100. Persons skilled in the art will recognize that ferromagnetic material 102 could be replaced with a magnet and second end 22 of body 20 and/or magnet 60 could be made of a ferromagnetic material for removably attaching apparatus 10 to the mobile device case.

In some embodiments, apparatus 10 includes a contact lens 30. Contact lens 30 may be used, for example, to modify the optics of a camera viewing a subject's skin (e.g. contact lens 30 may provide magnification) and/or to press three-dimensional features of skin to be imaged into one plane by pressing contact lens 30 against the skin. When contact lens 30 is being used a liquid (such as a gel) may optionally be applied to the surface of skin to be imaged. Contact lens 30 may be disposable. In some embodiments, contact lens 30 does not modify the camera optics and simply provides a window through which skin or other objects may be imaged. Such a window may provide a clean or sterile surface for contact with a subject's skin and/or prevent a gel or liquid applied to the subject's skin from contaminating the rest of apparatus 10 and/or press on the skin to be imaged.

Contact lens 30 may be removably attachable to first end 21 of body 20. In some embodiments, contact lens 30 is removably attached to first end 21 using one or more magnets. Persons skilled in the art will recognize that contact lens 30 may be removably attached to first end 21 using other means conventionally known. For example, contact lens 30 may be threadably secured, clipped, or snap-fit to first end 21 of body 20. In the example embodiment shown in FIGS. 1 and 2, contact lens 30 is removably attachable to first end 21 via a ferromagnetic ring 31 secured to an inner surface 33 of contact lens 30 adjacent to an edge 32. First end 21 of body 20 defines a rim 26 (see FIG. 7) concentric about aperture 23 for supporting a magnetic ring 27. Ferromagnetic ring 31 is complimentarily sized and shaped to magnetically attract and attach to magnetic ring 27 when contact lens 30 contacts first end 21.

Persons skilled in the art will recognize that ferromagnetic ring 31 could be replaced with a magnet and rim 26 and/or magnetic ring 27 could be made of a ferromagnetic material for removably attaching contact lens 30 to first end 21.

Contact lens 30 may be made of a light-transmitting material such as a polymeric clear plastic material and/or a glass material (such as quartz). In some embodiments, contact lens 30 does not substantially interfere and/or interact with light passing therethrough (e.g. contact lens 30 may serve a s a window). In some embodiments, contact lens 30 magnifies, diffuses, and/or filters light that passes through it.

Contact lens 30 may optionally include a colour palette (not shown). The colour palette may be used for colour calibrating a mobile device by measuring and/or adjusting the colour response of the device to the palette. The colour palette may, for example, comprise small patches of a number of selected known colours located around a periphery of contact lens 30 or on a mounting portion of contact lens 30 within a field of view of a camera of a mobile device.

Contact lens 30 may optionally include a scale reference such as a ruler, grid, scale length or the like that is in the field of view of a camera.

The optical system of apparatus 10 includes a light guide for collecting light from a mobile device light source and uniformly distributing the light to illuminate an object to be imaged. The optical system may further include a light cap for mixing light emitted by the light guide.

In some embodiments, the optical system includes a first light guide (e.g. light guide 80) arranged to collect light from the light source and a second light guide (e.g. light guide 110) arranged to uniformly distribute the light from the first light guide to illuminate an object (e.g. a skin lesion). The optical system may further include a light cap arranged to mix light emitted by the second light guide.

Figure 5:
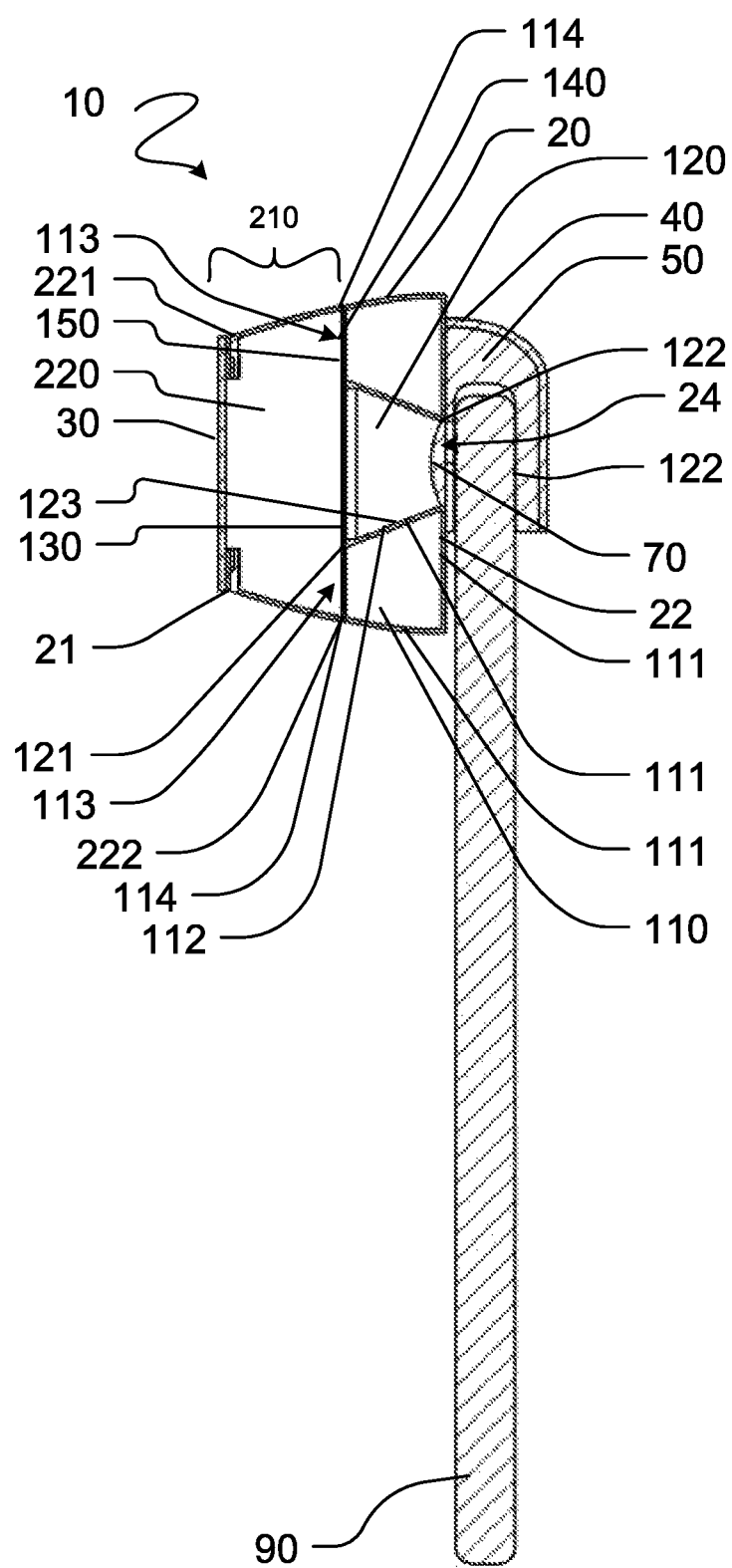
FIG. 5 is a side elevation cross-sectional view of the apparatus shown in FIG. 3.
Figure 7:
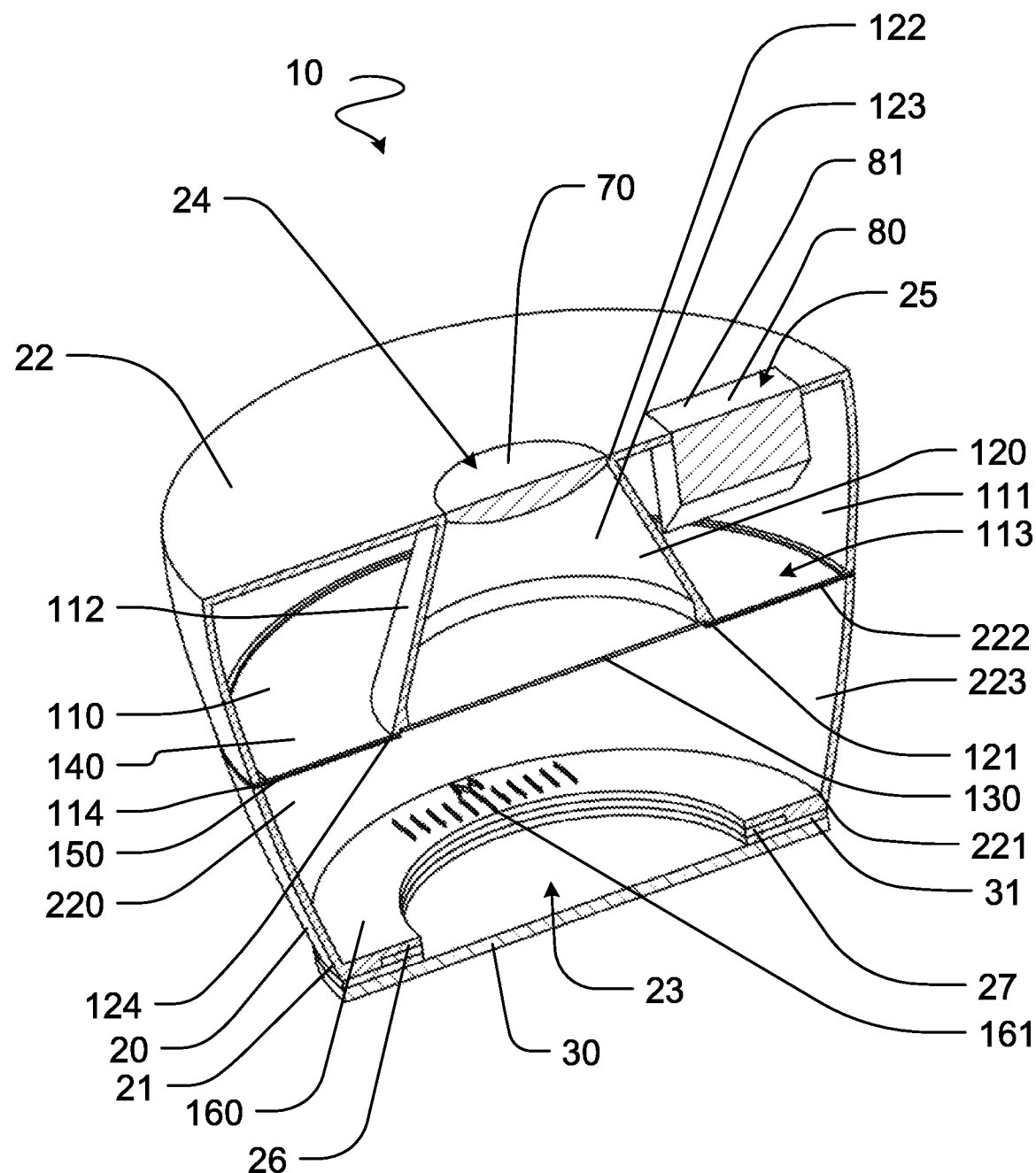
FIG. 7 is a perspective cross-sectional view of an apparatus for imaging skin according to an example embodiment of the present invention.
Figure 8:
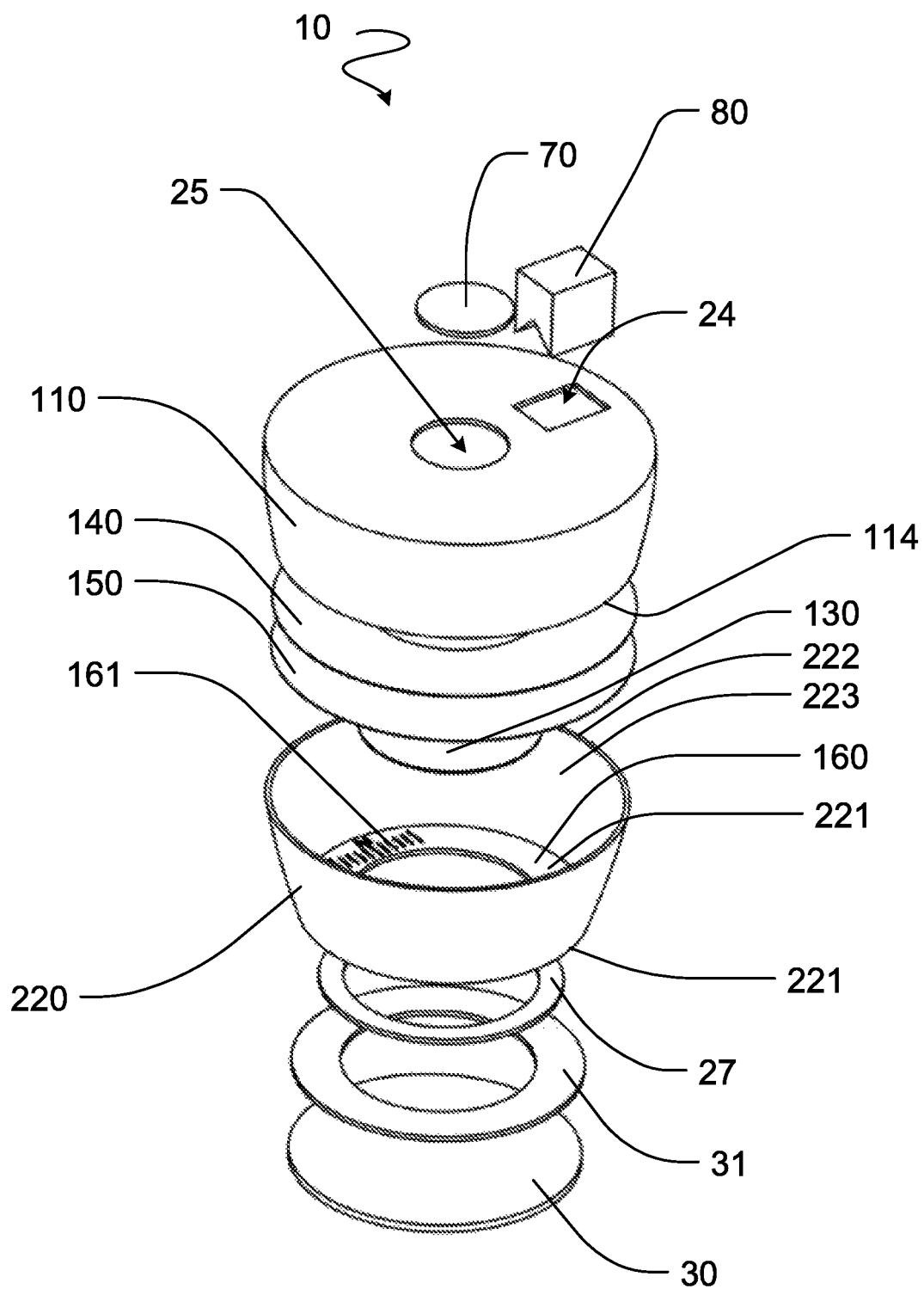
FIG. 8 is an extended view of the apparatus shown in FIG. 7.

In the example embodiment shown in FIGS. 5, 7, and 8, the optical system includes a beam splitter (e.g. prism light guide 80 or light reflector 170), a light guide 110, and a light cap 220 for illuminating an object to be imaged with light from a mobile device light source.

Light guide 80 may be positioned in aperture 25 of body 20 to collect light from the mobile device light source and to deflect the light sideways for distribution. For example, light may enter light guide 80 generally at right angles to the back of a mobile device and light guide 80 may redirect the light so that it exits light guide 80 generally parallel to the back of the mobile device. Such redirection helps to avoid forming a bright spot and accordingly helps to distribute light more uniformly within the light guide 110.

Figures 11, 12:
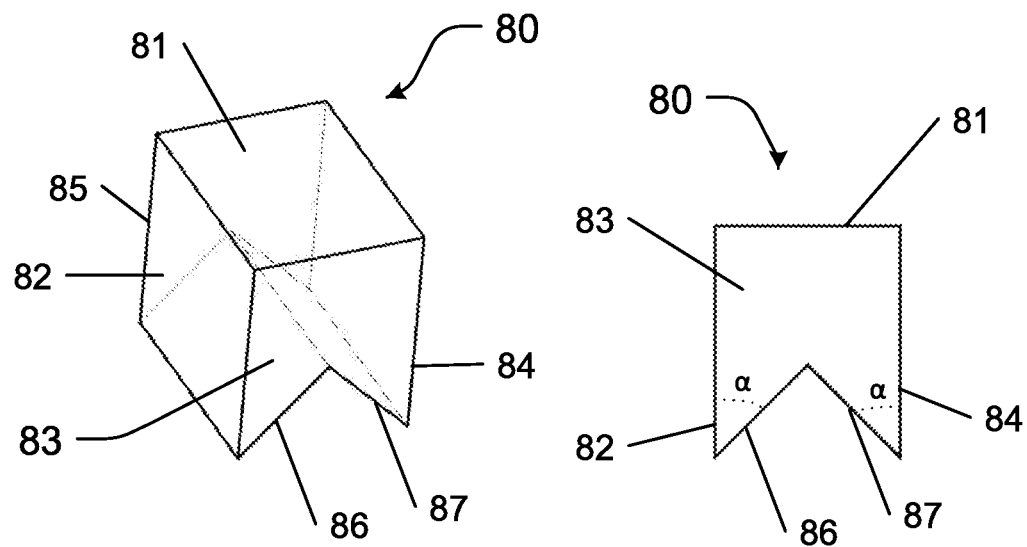
FIG. 11 is a perspective view of a prism light guide according to an example embodiment of the present invention.
FIG. 12 is a front plan view of the light guide shown in FIG. 11.

Deflection of light may be achieved through any of a range of different mechanisms. In the example embodiment shown in FIGS. 7, 8, 11, and 12, light guide 80 comprises a prism structure, which deflects light sideways by way of total internal reflection (TIR). When light guide 80 is positioned in aperture 25, a top surface 81 of prism light guide 80 faces outwardly from body 20 and surfaces 82, 83, 84, 85, 86, and 87 of light guide 80 are embedded inside body 20. A significant amount of the light rays emitted by the mobile device light source hit surfaces 82, 83, 84, or 85 where they experience total internal reflection and thus remain within light guide 80. Surfaces 82 and 86 and surfaces 84 and 87 form an angle α, as best seen in FIG. 12.

Depending on the angles of incidence of the light rays emitted by the light source, light rays that hit surfaces 86 or 87 will either exit light guide 80 or undergo total internal reflection. Light rays that are reflected internally by surfaces 86 and 87 are deflected at right angles and thus exit light guide 80 by way of side surfaces 82 and 84 respectively. The amount of light that is reflected by surfaces 86 and 87 in this direction (e.g. some reflected light rays travel approximately parallel to surface 81 after they are reflected) depends on angle α. To optimize the amount of light that is deflected sideways, an angle γ may be determined. Angle γ, which is based on the angular distribution of the mobile device light source, refers to the angle (or a range of angles, for example between about 0° to about 20°) chosen such that at least about 50%, preferably at least about 60%, more preferably at least about 70%, of the light rays from the mobile device light source falls within that range. Based on angle γ, angle α may be selected so that most or all light rays that enter light guide 80 with angles of incidence in the range of −γ to +γ (or the range from an angle x to the angle x+γ) are deflected toward the side faces of light guide 80.

Light guide 80 may be made of any clear light-transmitting material such as clear plastic or clear glass. Persons skilled in the art will recognize that prism light guide 80 may have any geometric shape, size, and/or configuration that achieves total internal reflection as described elsewhere herein. For example, surfaces 82, 83, 84, and 85 of light guide 80 may define an elliptical or circular cross-section. Where the cross-section of light guide 80 is elliptical or circular, aperture 25 is also elliptical or circular.

Figures 13, 14:
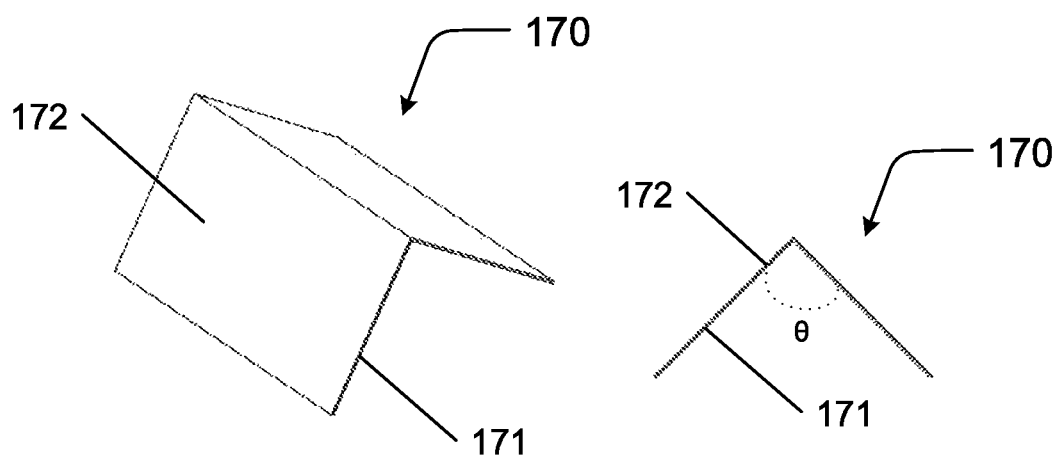
FIG. 13 is a perspective view a light reflector according to an example embodiment of the present invention.
FIG. 14 is a front plan view of the light reflector shown in FIG. 13.

In some other embodiments, light guide 80 is replaced with a light reflector, such as a V-shaped mirror 170 as shown in FIGS. 13 and 14. Light rays from the mobile device light source are reflected by the light reflector and delivered to the second light guide 110. V-shaped mirror 170 includes an inner surface 171 and an outer surface 172. Each surface 171 and 172 is made of a reflective material. By reflecting light, the light delivered to the second light guide is not focused in any one spot and, accordingly, may be uniformly distributed about the second light guide. In some embodiments, at least about 50% of light from the light source is reflected by outer surface 172, preferably at least 60% is reflected, more preferably at least about 70% is reflected. An angle θ defined by V-shaped mirror 170 may be selected to optimize the amount of reflected light distributed by light guide 110. To optimize the amount of light that is reflected, angle γ is determined as described elsewhere herein. Based on angle γ, angle θ may be selected so that light rays having angle γ are reflected in a direction that is almost parallel to the plane defined by end 22 of body 20. Thus, to optimize the amount of light uniformly distributed by mirror 170, angle θ is based on the angular distribution of the mobile device light source.

In the example embodiment shown in FIGS. 5, 7, and 8, light guide 110 is hollow, partially toroidal and is defined by the interior of body 20 adjacent to second end 22. Light guide 110, being partially toroidal, defines a conical interior 112 and an annular opening 113 at a first end 114 thereof. Annular opening 113 allows light to exit light guide 110 to illuminate an object to be imaged. Light guide 110 includes an interior surface 111 that is reflective. In some embodiments, interior surface 111 is at least about 90% reflective. In some embodiments, interior surface 111 comprises diffused reflective material or specular reflective material Light from mobile device light source 92 enters the light guide through aperture 25 and is deflected sideways by the beam splitter, either 80 or 170, and thus is uniformly distributed within light guide 110 before exiting light guide 110 via opening 113.

Figure 9:
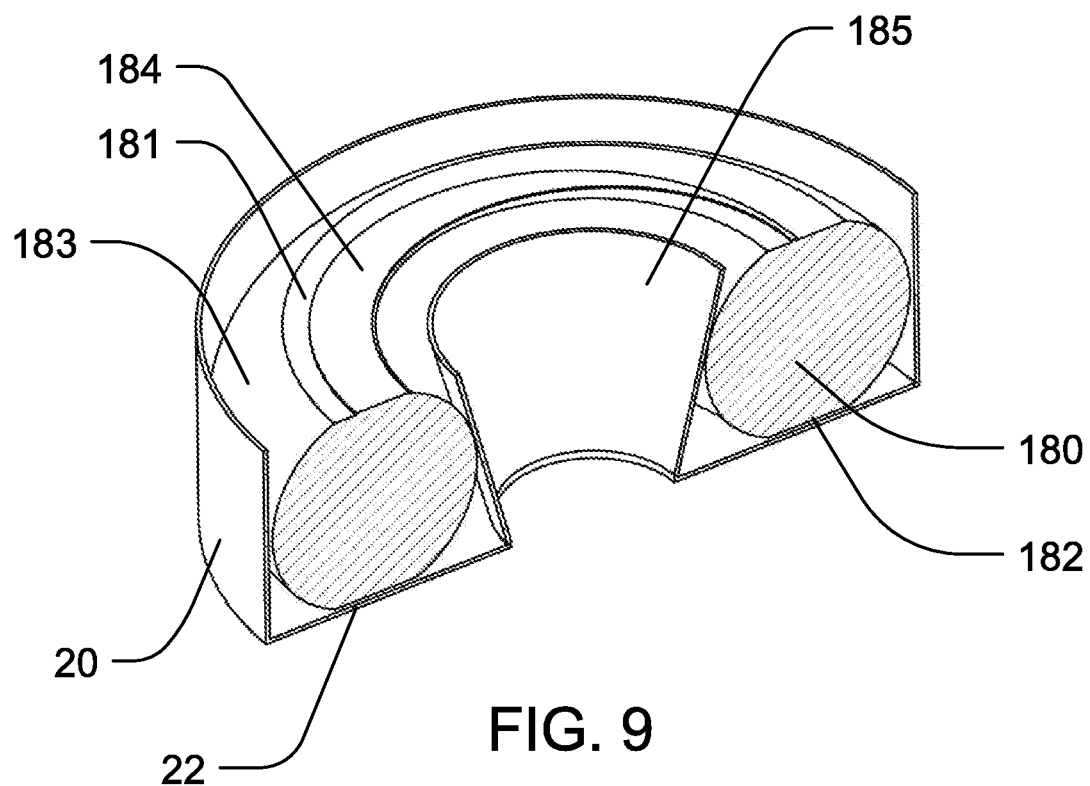
FIG. 9 is a cross-sectional view of a toroidal light guide according to an example embodiment of the present invention.

In some other embodiments, light guide 110 comprises a toroidal light guide, which may be solid or hollow. For example a solid toroidal light guide 180 is shown in FIG. 9. Light guide 180 is housed by body 20. Body 20 defines a conical interior 185. Lens 70 is housed in interior 185. Interior 185 can be substantially identical in shape to interior 112 of light guide 110 as described elsewhere herein. Light guide 180 includes a first surface 181 and a second surface 182 for collecting light from a mobile device light source. Light is emitted from light guide 180 via first surface 181 to enter light cap 220. Light from mobile device light source 92 enters the housing and is received into toroidal light guide 180. A significant amount of light that enters toroidal light guide 180 is totally internally reflected within light guide 180 and thus remains within light guide 180. To enhance the efficiency of light guide 180, an outer surface 183 of light guide 180 may be coated with a material having a refractive index that is higher than the refractive index of light guide 180. First surface 181 is, however, not coated with the higher refractive index material. An inner surface of body 20 housing light guide 180 may be coated with a reflective material. Light that enters light guide 180 from light source 92 is uniformly distributed within light guide 180 before exiting light guide 180 via first surface 181. Light guide 180 may be made of a solid piece of clear material, including but not limited to plastic and/or glass.

To control the amount of light that exits light guide 180 and/or to enhance uniform light distribution within light guide 180, light guide 180 may include a diffused surface 184 and/or a diffuser film (not shown) adjacent to first surface 181. A significant proportion of the light rays that hit diffused surface 184 do not undergo Total Internal Reflection and thus exit light guide 180. The area and/or texture of diffused surface 184 may vary with position along light guide 180. For example, the area of diffused surface 184 may increase as it gets further from aperture 25 of body 20.

This may be done in such a manner that the intensity of light emitted from light guide 180 is substantially uniform with position along light guide 180.

Figure 10:
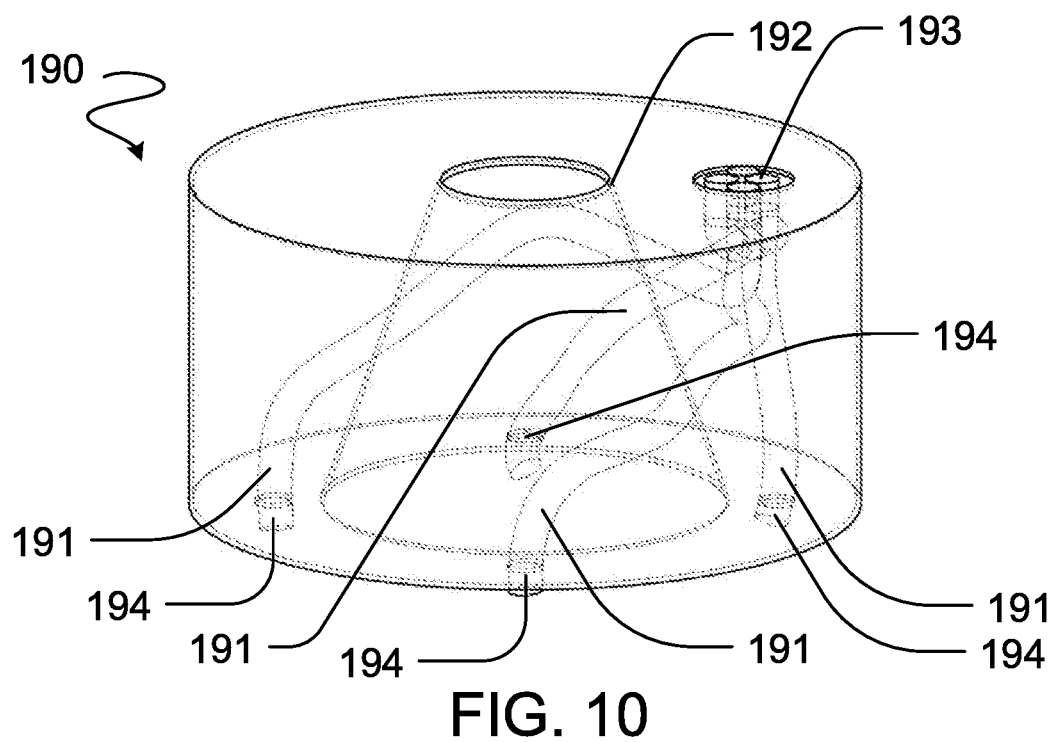
FIG. 10 is a perspective view of a fiber-optic light guide according to an example embodiment of the present invention.

In some other embodiments, light guide 110 is replaced with a fiber-optic light guide, for example fiber-optic light guide 190 shown in FIG. 10. Light guide 190 is housed by body 20 and includes a plurality of fibers 191 that merge at aperture 25 of body 20. A second end 193 of each fiber 191 captures light from the mobile device light source. Light is internally reflected within fibers 191 and delivered to a first end 194 of each fiber 191 opposed to second ends 193.

First ends 194 are circumferentially spaced about a conical interior 192 of fiber-optic light guide 190. Light is emitted from first ends 194 and enters light cap 220. Interior 192 may be substantially identical to interior 112 of light guide 110 as described elsewhere herein. Fiber-optic light guide 190 may be used where, for example, the distance between a mobile device attached to apparatus 10 and an object to be imaged is relatively large (for example, where the object to be imaged is the inner ear of a patient). Fibers 191 are made of a clear material, including but not limited to plastic and/or glass. Each fiber 191 may be coated with a material having a refractive index that is higher than the refractive index of fiber 191 to enhance the efficiency of light guide 190. An inner surface of body 20 housing light guide 190 may be coated with a reflective material.

Light cap 220 provides enough space for the light exiting from the light guide to mix and provide a uniform light for illuminating skin to be imaged. In the example embodiment shown in FIGS. 5, 7, and 8, light cap 220 is defined by the interior of body 20 adjacent to first end 21. Light cap 220 includes an inner surface 223 that is coated with a light-absorptive material, such as a matte black material, to prevent stray light from being reflected towards aperture 24. A distance 210 (see FIG. 5) between a first end 221 of light cap 220 and a second end 222 opposed to first end 221 is selected to uniformly mix the light emitted by aperture 113 of light guide 110 before the light exits light cap 220 via aperture 23 without significant intensity losses. Light cap 220 also blocks external light from interfering with the object to be imaged.

One advantage of blocking ambient light and illuminating the object to be imaged (e.g. a subject's skin) only with light from apparatus as described herein is that it can be assured that 'standard' lighting is used for illumination of each acquired image. This is important for ABCD image analysis (i.e. "Asymmetry, Border, Colors, and Dermoscopic structures").

When light cap 220 contacts the object it fixes the distance between the mobile device and the object and stabilizes the mobile device relative to the object. This facilitates obtaining high quality images of the object.

First end 221 of light cap 220 defines an annular surface 160 (see FIG. 7) that surrounds aperture 23. Annular surface 160 is at least partially in the field of view of the mobile device imaging system and, accordingly, may be used as a reference point to, for example, crop an acquired digital image. Annular surface 160 may include a reference ruler 161 and/or a reference colour chart or colour palette (not shown) to be used for calibration analysis and/or controlling exposure time. Where the object to be imaged, for example skin, is contacted by apparatus 10, the object may share approximately the same plane as ruler 161. Thus, ruler 161 may be used to measure the dimensions of the object and/or any feature of the object.

In some embodiments imaging software provided on a mobile device is configured to capture an image of ruler 161 from an image acquired using device 10 and to create an image overlay that includes the image of ruler 161. The image overlay may be displayed superposed on the desired image. Since the image of ruler 161 is obtained using the same optical system used to obtain an image of a subject's skin (or another object of interest) any magnification provided by the optical system is automatically accounted for. User interface controls may allow a user to position the image of ruler 161 in the image overlay at a desired position relative to the main image to allow measuring the dimensions of objects in the acquired image. In some embodiments the user interface controls allow a user to rotate the image overlay relative to the acquired image. Ruler 161 may be detected in an acquired image based on a known position of ruler 161 and/or by processing the acquired image to locate features characteristic of ruler 161 and/or by allowing a user to select the location of ruler 161 in the acquired image.

A reference colour palette (not shown) comprising one or more patches of known colours may be used to check the colour fidelity in images recorded by the mobile device. For example, images including the reference colour palette may be used to check for colour distortions that could occur if the mobile device over compensates a colour.

Light exiting light cap 220 via aperture 23 illuminates skin to be imaged with light that is suitable for imaging skin, including skin lesions and/or features below the surface of the skin. Light is reflected by the skin and re-enters apparatus 10 via aperture 23. The light travels through light cap 220 to a conduit, such as light conduit 120. Light conduit 120 delivers reflected light to a mobile device imaging system. Light conduit 120 may be defined by interior 112 of light guide 110. In the example embodiment shown in FIGS. 5, 7, and 8, light conduit 120 is conical and widens from a second end 122 adjacent second end 22 of body 20 to a first end 121 opposed to second end 122 adjacent light cap 220 such that the field of view of the mobile device imaging system is not blocked when apparatus 10 is attached to the mobile device. The extent of tapering of light conduit 120 may defines the field of view of apparatus 10. Light conduit 120 includes an inner surface 123 that is coated with a light-absorptive material to prevent stray light from reaching the mobile device imaging system. The outer surface of light conduit 120 (ie. interior 112) may be coated with a reflective material. Light conduit 120 blocks light from the mobile device light source from directly reaching the mobile device digital camera. Persons skilled in the art will recognize that light conduit 120 may be replaced with one or more light guides including, but not limited to, one or more optical fibers.

In some embodiments, light guide 120 includes a lens 70 at a second end 122 thereof. Lens 70 is concentrically aligned with a lens of a mobile device imaging system to minimize optical aberration when apparatus 10 is removably attached to the mobile device. The focal length and f-number of lens 70 may be selected such that a desired magnification of an object with minimal optical aberration is acquired. For example, in some embodiments, the focal length of lens 70 is between about 15 and about 20 mm and/or the optical magnification of lens 70 is between about 7× and 10×. Lens 70 may include, but is not limited to, a double-convex lens, a plano-convex lens, a Fresnel lens, a doublet lens, an achromatic lens, and a meniscus lens. Where magnification is not required of apparatus 10, lens 70 is not magnifying. Lens 70 may comprise a plurality of lenses. Lens 70 may be coated with an anti-reflection coating to improve image quality.

In some embodiments, apparatus 10 includes one or more filters. The one or more filters may be used to filter and/or polarize the light emitted by apparatus 10 and/or the light that is reflected by an object to be imaged. For example, as shown in the example embodiment illustrated in FIGS. 7 and 8, apparatus 10 includes a polarizer filter 130, a diffuser film 140, and a polarizer filter 150. Filter 130 is positioned at a first end 121 of light guide 120. Film 140 and filter 150 are positioned between light guide 110 and light cap 220 at opening 113. Film 140 faces second end 22 of body 20 and filter 150 faces first end 21 of body 20. In some embodiments, diffuser film 140 is used to diffuse light emitted by light guide 110. Diffuser film 140 may be used to reduce glare and/or increase the uniformity of light distribution.

In some embodiments, polarizer filter 150 polarizes light emitted by light guide 110. Polarizer filter 150 may be a linear polarizer or a circular polarizer (for example, a filter that polarizes light in the clockwise or counterclockwise direction). In some embodiments, polarizer filter 130 is used to filter unwanted light rays as described elsewhere herein. Polarizer filter 130 is of the same type as polarizer filter 150 (e.g. polarizer filters 130 and 150 may both be circular polarizers or may both be linear polarizers).

Light emitted from apparatus 10 illuminates skin to be imaged. Light is reflected by the skin as specular reflection and/or by diffuse reflection. Light rays that are reflected from the surface of an object via specular reflection may create glare in the acquired image. Specular reflected light often causes the imaged skin to appear shiny. Specular reflected light interferes with the acquisition of an image showing detailed features of the skin. Specular reflected light tends to have substantially the same polarization as the incident light emitted by apparatus 10. In contrast, diffused light is not polarized. Since skin is partially translucent, some light hitting the surface of the skin is reflected as diffuse light by the skin's deeper layers. Diffuse light may contain useful information about the skin and its features. Diffused reflected light passes through filter 130. Filter 130 may be used to substantially block specular reflected light rays, remove glare, and/or acquire a digital image of a feature below the surface of skin. For example, if filter 150 is a linear polarizer, then to block specular reflected light rays, filter 130 may be set with its polarization axis rotated 90° relative to that of filter 150. If filter 150 is a circular polarizer that polarizes light in the clockwise direction, then to block specular reflected light rays, filter 130 can be a circular polarizer that polarizes light in the counterclockwise direction. If filter 150 is a circular polarizer that polarizes light in the counterclockwise direction, then to block specular reflected light rays, filter 130 can be a polarizer that polarizes light in the clockwise direction. Where specular reflected light is not problematic, filter 130 may not be required and may be omitted.

In some embodiments, apparatus 10 may include a filter (not shown) for providing structured precision lighting to the object to be imaged. Light reflected by the object may have a pattern that differs from the pattern of the structured precision lighting emitted by apparatus 10. This pattern may be compared to that of the emitted light to measure and/or analyze three-dimensional characteristics of the imaged skin such as skin wrinkle.

To remove the glare reflection from the surface of imaged skin, a gel or other liquid may be applied to the surface of the skin. The gel or liquid may be used in addition to or alternatively to filters (such as filters 130 and 150) for removing glare. Contact lens 30 may be attached to apparatus 10 as described elsewhere herein and may function to protect apparatus 10 from the gel/liquid. Contact lens 30 attached to apparatus 10 is pressed into the gel/liquid and an image is acquired. Contact lens 30 may be disposed of following use.

Figure 3:
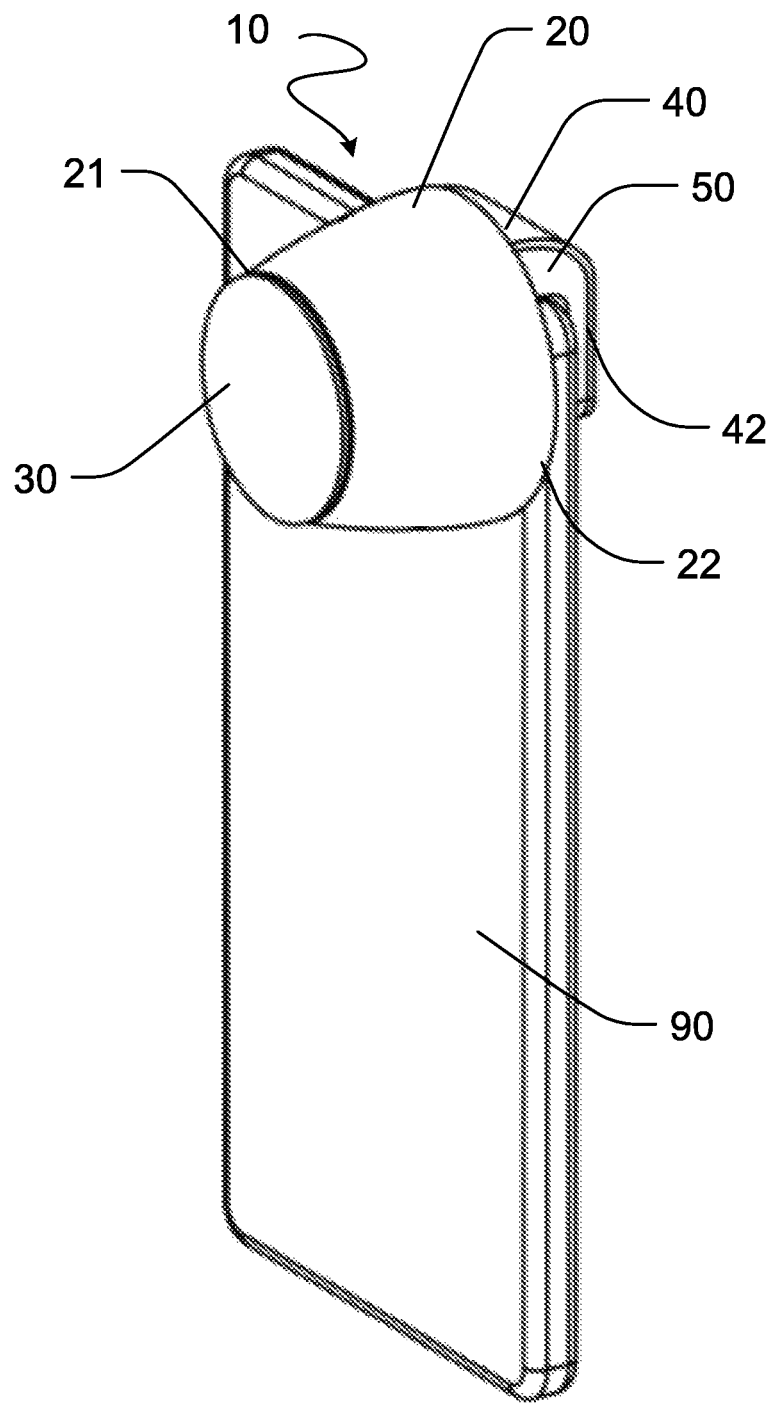
FIG. 3 is a front perspective view of the apparatus shown in FIG. 1, wherein the apparatus is removably attached to a mobile device.
Figure 4:
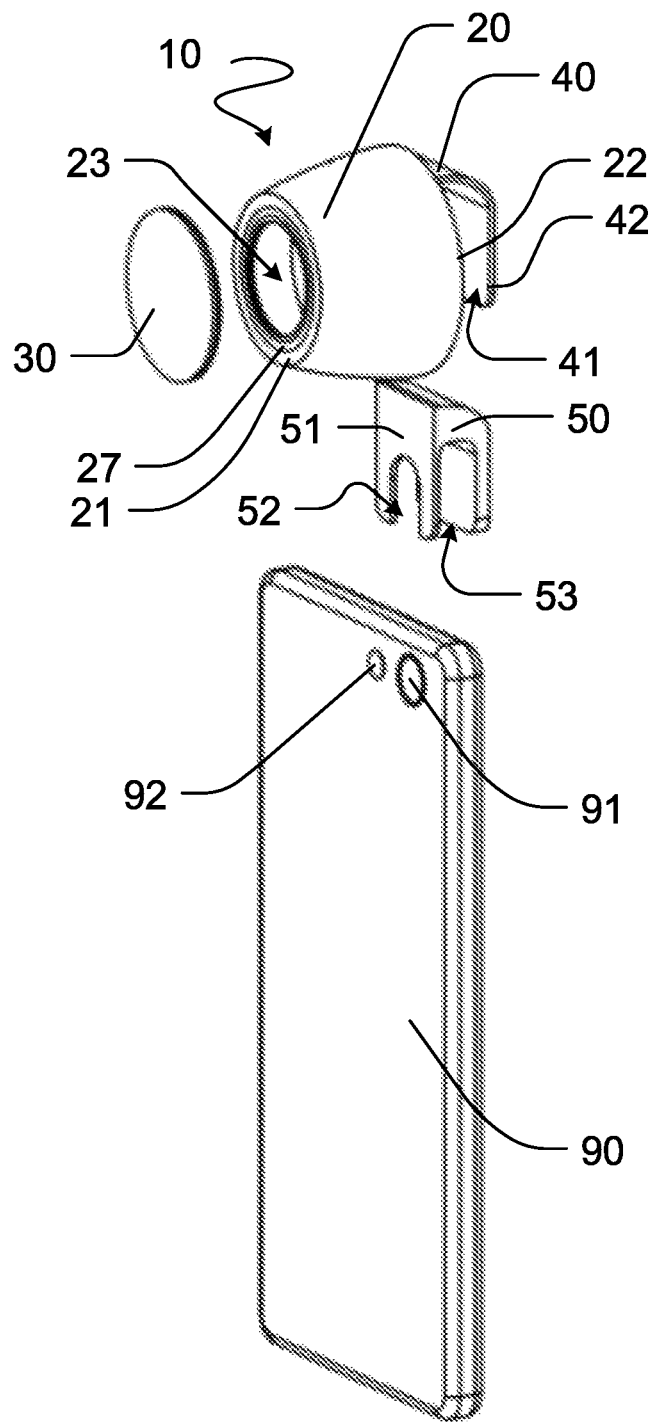
FIG. 4 is an extended front perspective view of the apparatus shown in FIG. 3.

To acquire a high quality and/or magnified digital image, apparatus 10 is attached to a mobile device, such as mobile device 90 shown in FIGS. 3, 4, and 5, as described elsewhere herein. Light from a light source 92 of the mobile device is collected and internally reflected by light guide 80. Light received by light guide 110 from light guide 80 is uniformly distributed before it enters light cap 220. In some embodiments, the light travels through polarizer filter 150 and/or diffuser film 140 before entering light cap 220. The light mixes uniformly within light cap 220 before exiting apparatus 10 through aperture 23. Light that is reflected by the object to be imaged re-enters apparatus 10 through aperture 23 and enters light conduit 120 via light cap 220. In some embodiments, the light travels through filter 130 before entering light conduit 120. Light exiting apparatus 10 via aperture 24 enters the mobile device digital camera via a lens 91. In some embodiments, light travels through lens 70 before exiting light conduit 120. The mobile device acquires an image of the skin as is conventionally known.

Figure 15:
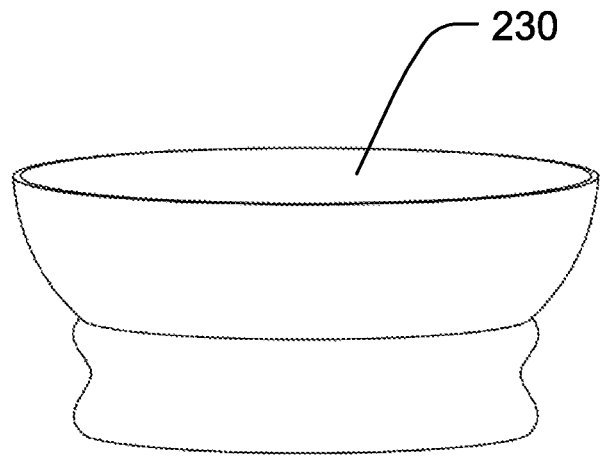
FIG. 15 is a perspective view of an eye cap according to an example embodiment of the present invention.

To acquire a digital image of an eye, an eye cap 230 (see FIG. 15) may be removably attached to first end 21 of apparatus 10. Eye cap 230 may be removably attachable to apparatus 10 in a substantially identical fashion as contact lens 30 as described elsewhere herein. Eye cap 230 may be made of a flexible, elastic material that comfortably fits around the eye.

Figure 16:
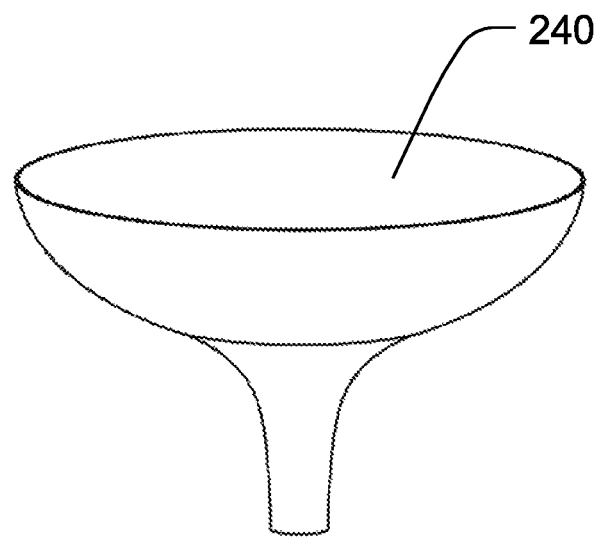
FIG. 16 is a perspective view of an ear cap according to an example embodiment of the present invention.

To acquire a digital image of an inner ear, an ear cap 240 (see FIG. 16) may be removably attached to first end 21 of apparatus 10. Ear cap 240 may be removably attachable to apparatus 10 in a substantially identical fashion as contact lens 30 as described elsewhere herein.

Ear cap 240 is configured to fit into the inner ear of a human and/or animal.

Where eye cap 230 or ear cap 240 is removably attached to apparatus 10, apparatus 10 lacks contact lens 30 and light cap 220.

Computer software may be used with apparatus 10 to acquire, store, process, manage, and/or manipulate digital images. The software may be stored on a mobile device and/or a desktop computer. The software may be used to improve image quality. For example, the software may be used to control illumination and/or colour, bring an object to be imaged into focus, and/or correct image defects (for example, by making corrections for artifacts such as oil or gel bubbles, hair, and/or shadows). The software may use the mobile device's graphics processing unit and/or central processing unit to process images in real-time. The software may check the border of aperture 23 and alert a user if apparatus 10 is being improperly used (e.g. because apparatus 10 is not properly aligned to the camera of a mobile device).

Where apparatus 10 is used to digitally image skin, the software may be used to label, archive, monitor, and/or analyze skin features including, but not limited to, lesions, psoriasis, eczema, wounds, and wrinkles. For example, the software may be used to monitor changes in the height, diameter, and/or pigmentation of such skin features by comparing two or more digital images acquired at different times. The appearance and/or disappearance of skin features may be monitored in this way.

In some embodiments, the software is configured to process image data to calculate an ABCD (i.e. "Asymmetry, Border, Colors, and Dermoscopic structures") score and/or other conventional dermoscopic criteria. Such processing may be used to analyze skin features such as moles. The ABCD value may be used to determine if the mole is prone to be benign or malignant and if further treatment and examination is recommended. The software may also recommend a personalized skin care and/or treatment plan. The software can also generate a report to be sent to a specialist for further examination and monitoring. This data can be highly helpful for detecting skin cancer or other skin diseases at early stage.

The software may provide a database of images for comparison and diagnostic purposes. Diagnosis may be performed automatically by the software and/or performed by a user or the user's physician.

In some embodiments, the software may be used to acquire one or more digital images (including, but not limited to, panoramic images) to generate a two-dimensional or three-dimensional map of a human and/or animal body, body part, and/or skin feature.

In some embodiments, the software provides a virtual image or 'ghost' of a human and/or animal body and/or body part that can be used to guide the user as the user acquires images (including, but not limited to, panoramic images) of the body and/or body part using apparatus 10. In some embodiments, a drone or a stationary device may be used with apparatus 10 to acquire the digital images.

As described elsewhere herein, digital images may be acquired with or without contacting the object to be imaged. The acquired digital images may be polarized, cross-polarized, or non-polarized.

Persons skilled in the art will recognize that:
- the position of the lens and light source of different mobile devices may differ. Apparatus 10 may be configured to accommodate a variety of lens and light source positions. For example, light guide 80 (or mirror 170) may be sized, shaped, and/or configured to accommodate mobile devices having a variety of lens and light source positions. Where the distance between the lens and light source of a mobile device is large, a larger light guide 80 (or mirror 170) may be used.
- body 20 may have other shapes, sizes, and configurations than those described elsewhere herein. For example, body 20 may be rectangular.
- by using the light source of the mobile device, apparatus 10 does not require an internal light source, power supply, or printed circuit board.
- apparatus 10 has many different applications, including but not limited to applications in clinical lab examinations (such as dermatology, trichology, nail circulation, iridology, and veterinary lab examinations), in science and education (such as entomology, botany, archeology, and minerology), and in quality control and inspection (such as in circuit boards, printing, jewelry, and collectibles). Accordingly, unless the context dictates otherwise, "apparatus" (as used herein) refers to an optical system, the use of which should not be limited to dermoscopic applications.

Interpretation of Terms

Unless the context clearly requires otherwise, throughout the description and the claims:
- "comprise", "comprising", and the like are to be construed in an inclusive sense, as opposed to an exclusive or exhaustive sense; that is to say, in the sense of "including, but not limited to";
- "connected", "coupled", or any variant thereof, means any connection or coupling, either direct or indirect, between two or more elements; the coupling or connection between the elements can be physical, logical, or a combination thereof;
- "herein", "above", "below", and words of similar import, when used to describe this specification, shall refer to this specification as a whole, and not to any particular portions of this specification;
- "or", in reference to a list of two or more items, covers all of the following interpretations of the word: any of the items in the list, all of the items in the list, and any combination of the items in the list;
- the singular forms "a", "an", and "the" also include the meaning of any appropriate plural forms.

Words that indicate directions such as "vertical", "transverse", "horizontal", "upward", "downward", "forward", "backward", "inward", "outward", "left", "right", "front", "back", "top", "bottom", "below", "above", "under", and the like, used in this description and any accompanying claims (where present), depend on the specific orientation of the apparatus described and illustrated. The subject matter described herein may assume various alternative orientations. Accordingly, these directional terms are not strictly defined and should not be interpreted narrowly.

Where a component (e.g. a substrate, assembly, device, manifold, etc.) is referred to above, unless otherwise indicated, reference to that component (including a reference to a "means") should be interpreted as including as equivalents of that component any component which performs the function of the described component (i.e., that is functionally equivalent), including components which are not structurally equivalent to the disclosed structure which performs the function in the illustrated exemplary embodiments described herein.

Specific examples of systems, methods, and apparatus have been described herein for purposes of illustration. These are only examples. The technology provided herein can be applied to systems other than the example systems described above. Many alterations, modifications, additions, omissions, and permutations are possible within the practice of this invention. This invention includes variations on described embodiments that would be apparent to the skilled addressee, including variations obtained by: replacing features, elements and/or acts with equivalent features, elements and/or acts; mixing and matching of features, elements and/or acts from different embodiments; combining features, elements and/or acts from embodiments as described herein with features, elements and/or acts of other technology; and/or omitting combining features, elements and/or acts from described embodiments.

The invention claimed is:

1. An apparatus for use with a mobile device, the apparatus comprising:
a body having a first end defining a first aperture and a second end opposed to the first end, the second end defining a lens aperture and a light guide aperture, wherein the lens aperture is configured to align with a mobile device lens and the light guide aperture is configured to align with a mobile device light source when the apparatus is removably attached to the mobile device, the body comprising an optical system for illuminating an object to be imaged and a light conduit for delivering light reflected by the object to the mobile device lens; and
a connector connected to the body, the connector operable for removably attaching the apparatus to the mobile device, wherein the optical system comprises a beam splitter and a light guide, the beam splitter positioned to receive light from the mobile device light source by way of the light guide aperture and operative to split and deflect the light received from the mobile device light source into a plurality of deflected light beams and to direct first and second deflected light beams into the light guide in substantially opposite directions that are substantially parallel to a plane defined by the first end of the body, the light guide extending around the light conduit and configured to receive the plurality of light beams from the beam splitter and to uniformly distribute the light to illuminate the object to be imaged.

2. The apparatus according to claim 1 wherein the beam splitter is positioned in the light source aperture.

3. The apparatus according to claim 1 wherein the beam splitter comprises a prism light guide.

4. The apparatus according to claim 1 wherein the beam splitter comprises a light reflector.

5. The apparatus according to claim 4 wherein the light reflector comprises a V-shaped mirror.

6. The apparatus according to claim 1 wherein the light guide extends in a ring around the light conduit.

7. The apparatus according to claim 1 wherein the light guide comprises a toroidal light guide configured to distribute light received from the beam splitter uniformly along a surface facing the first aperture.

8. The apparatus according to claim 7 wherein the toroidal light guide comprises a reflective interior surface and an annular opening for allowing light to exit therefrom.

9. The apparatus according to claim 7 wherein the toroidal light guide comprises a first flat surface for allowing light to exit therefrom and a second flat surface for capturing light from the beam splitter.

10. The apparatus according to claim 7 wherein the toroidal light guide comprises a ring-shaped body of a material having a first index of refraction and an outer surface coated with a material having an index of refraction that is greater than the first index of refraction.

11. The apparatus according to claim 9 wherein the toroidal light guide comprises one or more of a diffused surface and a diffuser film adjacent to the first flat surface.

12. The apparatus according to claim 1 wherein the body further comprises a light cap, wherein a distance between a first end of the light cap and a second end of the light cap opposed to the first end is selected to mix the light from the optical system uniformly.

13. The apparatus according to claim 12 wherein an interior surface of the light cap is coated with a light-absorptive material.

14. The apparatus according to claim 1 wherein an interior surface of the light conduit is coated with a light-absorptive material.

15. The apparatus according to claim 1 further comprising a mobile device case, wherein the connector includes a magnetic piece that is magnetically attracted to the case for removably attaching the apparatus to the case.

16. The apparatus according to claim 15 wherein the case defines an aperture configured to align with the mobile device lens and the mobile device light source when the mobile device is inserted into the case.

17. The apparatus according to claim 1 further comprising at least one filter.

18. The apparatus according to claim 17 wherein the at least one filter comprises one or more of a diffuser film and a polarizer filter.

19. The apparatus according to claim 17 wherein the at least one filter comprises a filter having spatially-varying light transmission properties for providing structured precision lighting.

20. The apparatus according to claim 1 wherein the connector defines an opening for receiving a body of the mobile device and an adapter configured to be received in the opening, the adapter dimensioned to grip the body of the mobile device.

* * * * *